United States Patent
Maitra et al.

(10) Patent No.: US 6,579,519 B2
(45) Date of Patent: Jun. 17, 2003

(54) SUSTAINED RELEASE AND LONG RESIDING OPHTHALMIC FORMULATION AND THE PROCESS OF PREPARING THE SAME

(75) Inventors: Amarnath Maitra, Delhi (IN); Ajay Kumar Gupta, Delhi (IN); Dipak Majumdar, New Delhi (IN); Sumit Madan, New Delhi (IN)

(73) Assignee: Registrar, University of Delhi, Delhi (IN)

( * ) Notice: Subject to any disclaimer, the term of this patent is extended or adjusted under 35 U.S.C. 154(b) by 0 days.

(21) Appl. No.: 09/954,722

(22) Filed: Sep. 18, 2001

(65) Prior Publication Data

US 2002/0064513 A1 May 30, 2002

(30) Foreign Application Priority Data

Sep. 18, 2000 (IN) ..................................... 845/DEL/2000
Sep. 26, 2000 (IN) ..................................... 871/DEL/2000

(51) Int. Cl.$^7$ ..................... A61K 31/74; A01N 25/00; A01N 25/32
(52) U.S. Cl. ................ 424/78.04; 424/78.04; 424/405; 424/406; 424/486; 424/489
(58) Field of Search ................ 424/456, 405, 424/78.08, 489, 78.04

(56) References Cited

U.S. PATENT DOCUMENTS

| | | | | | |
|---|---|---|---|---|---|
| 4,919,939 A | * | 4/1990 | Baker | ......................... | 424/493 |
| 5,053,228 A | * | 10/1991 | Mori et al. | ................. | 424/486 |
| 5,091,188 A | * | 2/1992 | Haynes | ........................ | 424/450 |
| 5,449,513 A | * | 9/1995 | Yokoyama et al. | ...... | 424/78.08 |
| 5,547,612 A | * | 8/1996 | Austin et al. | ........... | 134/22.19 |

* cited by examiner

*Primary Examiner*—Thurman K. Page
*Assistant Examiner*—Micah-Paul Young
(74) *Attorney, Agent, or Firm*—Sidley Austin Brown & Wood LLP

(57) ABSTRACT

The present invention relates to sustained release and long residing opthalmic formulation having thermosensitivity, mucoadhesiveness, hydro gel properties and small particle size. The said formulation comprises micelle solution of random block co-polymer having a hydrophobic component and a hydrophillic component of general formula —(X+Y+Z-)$_m$, and at least one hydrophobic drug with the block co-polymer solution. The invention also provides a process of preparing said formulation.

38 Claims, 3 Drawing Sheets

Figure 1:
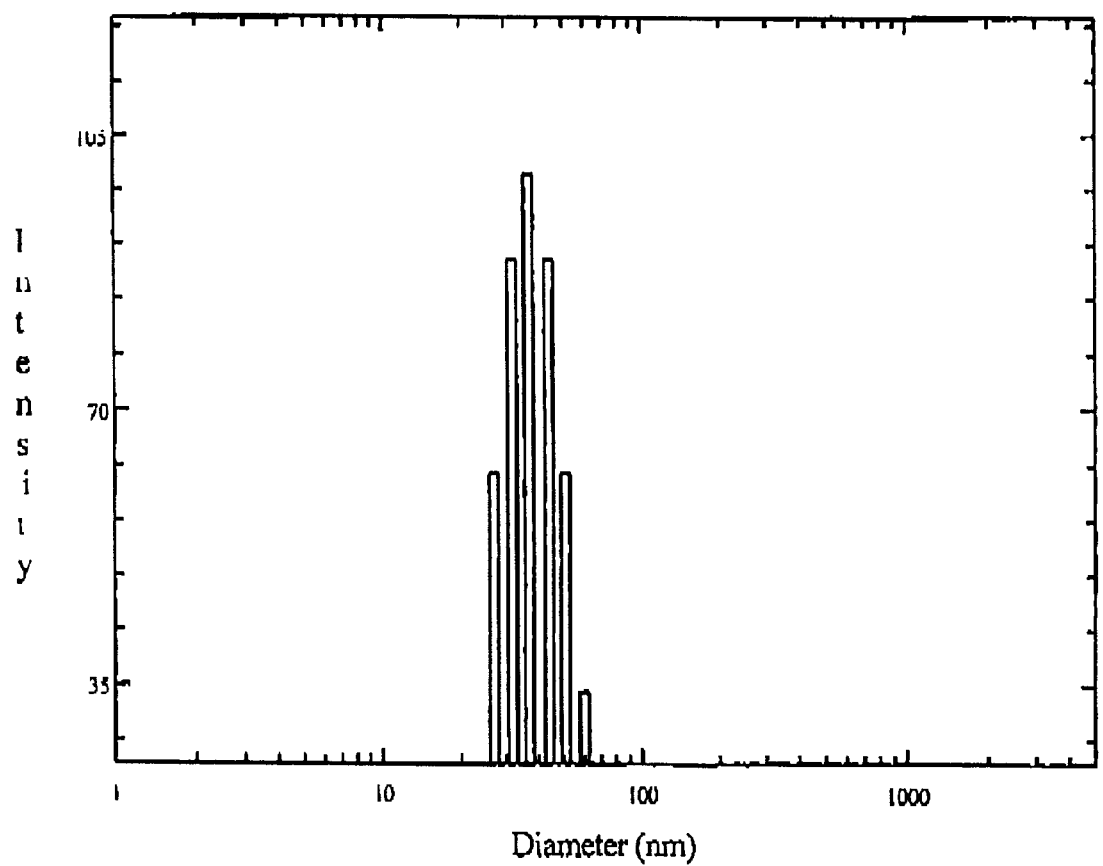

SUSTAINED RELEASE AND LONG RESIDING OPHTHALMIC FORMULATION AND THE PROCESS OF PREPARING THE SAME

FIELD OF THE INVENTION

The present invention relates to a sustained release and long residing ophthalmic formulation and the process of preparing the same.

BACKGROUND OF THE INVENTION

Medication of the eyes is done for two purposes—to treat the outside of the eyes for such infections as conjunctivitis, blepharitis, keratitis sicca etc and to provide intraocular treatment through the cornea for diseases such as glaucoma or uveitis. Most ocular diseases are treated with topical application of solutions administered as eye drops. One of the major problems encountered with the topical delivery of ophthalmic drugs is the rapid and extensive precorneal loss caused by drainage and high tear fluid turn over. After instillation of an eye-drop, typically less than 2–3% of the applied drug penetrates the cornea and reaches the intraocular tissue, while a major fraction of the instilled dose is often absorbed systematically via the conjunctiva and nasolacrimal duct. Another limitation is relatively impermeable corneal barrier that limits ocular absorption.

Because of the inherent problems associated with the conventional eye-drops there is a significant efforts directed towards new drug delivery systems for ophthalmic administration such as hydrogels, micro- and nanoparticles, liposomes and collagen shields. Ocular drug delivery is an approach to controlling and ultimately optimizing delivery of the drug to its target tissue in the eye. Most of the formulation efforts aim at maximizing ocular drug absorption through prolongation of the drug residence time in the cornea and conjunctival sac as well as to slow drug release from the delivery system and minimizing precorneal drug loss.

To solve the above mentioned problem associated with the ocular delivery of drugs. WO 9405257 A1 940317 discloses a method for preparing a bioerodible drug delivery vehicle composed of solid polymeric matrix formed from derivatised cellulose and methacrylic acid copolymer and incorporating ophthalmic drugs in it. The inventors have demonstrated that such formulation when instilled in eyes the polymeric materials bio-erodes and dispenses the incorporated drug on the cornea surface. However, the problem always associated with the use of such bulk gel is the blurring effect and bio-compatibility of the polymeric material. Moreover, the long residence time and sustained release of drug on cornea surface have not been achieved.

There have been reported other studies on the use of co-polymeric materials as earners for ophthalmic drugs and particularly noteworthy are the attempts to incorporate hydrophobic drugs into the hydrophobic core of the copolymer micelles. The pharmaceutical efficacy of these formulations depends on the specific nature and properties of the co-polymeric materials.

For example, EP 0744938 A1 961204 discloses sustained release liquid aqueous ophthalmic delivery system. The method provides a slow and sustained release of treating agents. The polymer used was chitosan and was applied in the form of bulk material. However, it is difficult for such bulk polymer to penetrate the conceal membrane and the liquid formulation remain in the liquid form even at body temperature so that there exists every possibility to be washed away by tears. There also exists a problem of this formulation. The acidic pH of the liquid pH 3.0 to 6.2, is not very much patient compliance. The other patents with related formulation with chitosan is WO 9522315 A1 950824 and EP 0594760.

A1 940504 discloses a method for entrapping ophthalmic drugs in polyacryl acid polymer to obtain a fluid aqueous gel having a pH of between 6.5 and 8. The formulation is claimed to be useful for treating various pathological ocular conditions. This method, thus solves the potential mucoadhesive problem of the polymer by using poly-acrylic acid gels. However, pure polyacryl acid is so much sticky that a permanent polymer layer on the cornea surface may cause blurred vision. Moreover, being bulk gel, these polymeric composition may not have sufficient penetration and subsequently less bio-availability. The same is the comment for other patents: WO 9300887 A1 930121 and WO 9922713 A1 19990514 and WO 9405257 A1 940317.

There are reported studies on formulations of non-steroidal anti-inflammatory drugs (NSAID) using different carriers particularly directed towards oral delivery to avoid the adverse effects on the gastrointestinal tract.

A patent WO 93/25190 has disclosed surface modified NSAID nanoparticles by taking crystalline NSAID having surface modifier adsorbed on the surface thereof in an amount sufficient to maintain an effective average particle size of less than about 400 nm.

One patent, EP 0274870 A2 880720, has disclosed the micelles containing polyethoxylated nonionic surfactant as carrier for certain NSAIDs. Other patents. EP 0818992 A1 980121 and WO 9505166 A1 950223 disclose the similar type of micellar encapsulation of NSAIDs using cellular acetate phthalate and gelatin.

Another patent, WO 9702017 A1 970123 used hydrophilic poloxamer for encapsulating NSAIDs. These are some of the patents, which are mainly directed towards oral delivery formulations so that these NSAIDs cannot be exposed in GI tract. These formulations do not have any relevance to eye drop preparations.

To overcome the problem of blurred vision and poor bio-availability of drug by using bulk gel in ophthalmic formulations, it has been suggested that colloidal carriers would have better effect. Colloidal carriers which have been studied for ocular delivery are mainly liposomes and nanoparticles because of their extremely small size. The main limitation of liposomes as ocular drug delivery system is its surface charge. Positively charged liposomes seemed to be preferentially captured at the negatively charged corneal surface compared to neutral and negatively charged liposomes. Another limitation of liposomes is the instability of the lipid aggregates on the mucine surface. The vesicular aggregates of positively charged lipids are completely disintegrated on the negatively charged mucine membrane surface.

Nanoparticles as drug carriers for ocular delivery have been revealed to be more efficient than liposomes and in addition to all positive points of liposomes, these nanoparticles are exceptionally stable entity and the sustained release of drug can be modulated.

Some studies have been reported in the literature as well as patents on the use of nanoparticles carriers for encapsulating water insoluble drugs. For example, a U.S. Pat. No. 5,510,103 disclose the entrapment of water-insoluble drugs including NSAIDs in the hydrophobic core of polymeric micelles of different block copolymers. Another U.S. Pat.

No. 5,449,513 has also disclosed the use of various amphiphilic copolymers in the form of micelles to physically entrap water-insoluble drugs. The other patents of similar type are U.S. Pat. No. 5,510,103, U.S. Pat. No. 5,449,513, U.S. Pat. No. 5,124,151.

All these patents described the method of preparation of amphiphilic copolymers of random compositions of two or three different types of amphiphilic monomers and aggregating them in aqueous solutions and dissolving the water-insoluble drugs inside the hydrophobic core of these polymeric micelles. The properties of these copolymers are governed by the composition of them. But none of the polymers could comply the overall requirements of best ophthalmic formulation—hydrogel formation, mucoadhesiveness, thermosensitivity and small particle size—in a single formulation.

THE OBJECT AND SUMMARY OF THE INVENTION

The object of the present invention is to obviate the above-mentioned drawbacks and to provide a formulation having thermosensitivity, mucoadhesiveness, hydrogel properties and small particle size all together in a single composition.

Still further object of this invention is to provide sustained release and long residing ophthalmic formulation, so that the release of the entrapped drug can be controlled and the process of preparing the same.

To achieve the said objectives, this invention provides a sustained release and long residing ophthalmic formulation comprising:

micelle solution of block random co-polymer having a hydrophobic component and a hydrophilic component of general formula —(X+Y+Z-)$_m$, wherein m is an integer greater than 2, X is a monomer which will provide hydrogel formation properties of the co-polymer to reduce the irritability of the eye and is selected from vinyl group of compounds, Y is a monomer which will provide thermosensitivity properties of the co-polymer having a general formula $R_1$—$R_2$N—(C=O)—CH=CH$_2$, where $R_1$=a proton or $C_nH_{2n+1}$ in which n may have the value from 3 to 6 and $R_2$=alkyl group having chain length of $C_3$ to $C_6$ Z is a monomer which will provide mucoadhesiveness and pH-sensitivity properties to the co-polymer and is selected from acrylate based monomers.

and at least one hydrophobic drug with the said block co-polymer solution;

The said vinyl group of compounds is selected from vinyl pyrrolidone, vinyl alcohol, vinyl chloride or vinyl acetate.

Y is N-isopropyl acrylamide(NIPAAM)

The said acrylate based monomers is selected from acrylic acid or methyl methacrylate.

'm' lies in the range 10–4000.

The said drug is a hydrophobic ohphthalmic drug and is selected from the family of non steroidal anti inflammatory drug (NSAID).

The said NSAID drug is selected from 5-benzoyl (2,3 dihydro-1H pyrrolizone-1carboxylic acid); 1-(4 chlorobenzoyl)-5 methoxy-2-methyl-1H-indole-3acetic acid or N-(4-nitro-2 phenoxyphenyl) methanesulphonamide or a mixture of at least any two thereof.

The said drug used for entrapment is in solution or in powder form.

The said drug is hydrophobic.

The said polymerized micelles containing the hydrophobic drug have a size in the range of 10 nm–100 nm diameter The said polymerized micelles containing the hydrophobic drug have a size in the range of 10 nm to 50 nm.

The random block copolymers, made of amphiphilic monomers, are biocompatible and non-antigenic materials.

The optimum molar ratio of the combination of amphiphilic monomers X, Y and Z is 9.5%:85.7%:4.8% respectively from the point of view of mucoadhesiveness and thermosensitivity of the co-polymer.

The present invention further provides a process for preparing a sustained release and long residing ophthalmic formulation comprising the steps of:

preparing micelle solution of block random co-polymer having a hydrophobic component and a hydrophilic component of general formula —(X+Y+Z-)$_m$, wherein m is an integer greater than 2

X is a monomer which will provide hydrogel formation properties of the co-polymer to reduce the irritability of the eye and is selected from vinyl group of compounds Y is a monomer which will provide thermosensitivity properties of the co-polymer having a general formula $R_1$—$R_2$N—(C=O)—CH=CH$_2$, $R_1$=a proton or $C_nH_{2n+1}$ in which n may have the value from 3 to 6 and $R_2$=alkyl group having chain length of $C_3$ to $C_6$ Z is a monomer which will provide mucoadhesiveness and pH-sensitivity properties to the co-polymer and is selected from acrylate based monomers.

mixing at least one hydrophobic drug with the said block co-polymer solution;

subjecting the resulting mixture to stirring, heating, ultrasonic treatment, solvent evaporation or dialysis to physically incorporate the hydrophobic drug into the hydrophobic core of block co-polymeric micelle, and purifying the mixture to recover the sustained release and long residing ophthalmic formulation.

The said micelle solution of block copolymers is prepared by:

dissolving amphiphilic monomers in an aqueous medium to obtain micelles, adding aqueous solutions of cross-linking agent, activator and initiator into the said micelles, and subjecting the said mixture to polymerization in presence of an inert gas at 30° C.–40° C. till the polymerization of micelles is complete.

The said vinyl group of compounds is selected from vinyl pyrrolidone, vinyl alcohol, vinyl chloride or vinyl acetate.

Y is N-isopropyl acrylamide.

The said acrylate based monomers is selected from acrylic acid or methyl metharylate.

'm' lies in the range 10–4000.

The said purification is done by dialysis.

The said drug is non steroidal anti inflammatory drug (NSAID).

The said NSAID drug is selected from 5-benzoyl (2,3 dihydro-1H pyrrolizone-1 carboxylic acid) (keterolac); 1-(4 chlorobenzoyl)-5 methoxy-2-methyl-1H-indole-3acetic acid (indomethacin) or N-(4-nitro-2 phenoxyphenyl) methanesulphonamide (nimesulide) or a mixture thereof or a mixture of at least any two drugs.

The said polymerized micelles containing the hydrophobic drug have a size in the range of 10 nm–100 nm diameter.

The said polymerized micelles containing the hydrophobic drug have a size in the range of 10 nm to 50 nm.

The block copolymers, made of amphiphilic monomers, are biocompatible and non-antigenic materials.

The said drug used for entrapment is in solution form or in powder form.

The solvent used for dissolving the drug is selected from dimethylformamide (DMF), dimethylsulphoxide (DMSO), dioxane, chloroform, n-hexane, dichloromethane, ethylacetate, ethanol, methanol.

The said dialysis is carried out for 2–4 hours to eliminate unreacted monomers and free NSAID, if any, at the aqueous phase.

The said drug is in hydrophobic form.

The said cross-linking agent is a bifunctional vinyl derivative.

The said bifunctional vinyl derivative is N,N' methylene bis acrylamide.

The said initiators are peroxide derivatives or 2,2'-azo bis isobutyronitrile (AIBN).

The said peroxide derivatives are benzoyl peroxide, or perdisulphate salts like ammonium perdisulphate.

The said activator is ferrous ammonium sulphate (FAS).

The said inert gas is nitrogen or argon.

The optimum combination of amphiphilic monomers is Vinyl pyrrolidone (VP), N-isopropyl acrylamide (NIPAAM) and acrylic acid (AA) in the molar ratio 9.5%:85.7%:4.8%.

The temperature at which polymerization is carried out ranges between 20° C.–80° C.

The temperature at which polymerization is carried out ranges between 30° C.–40° C.

The block copolymer micelles composed of polyvinylpyrrolidone (which produces hydrogel to reduce the irritability of the eye), poly-N-isopropylacrylamide (pNIPAAM) (which renders thermosensitivity) and polyacrylic acid (which renders mucoadhesiveness) to the polymeric micelles. The copolymer is having an inner hydrophobic core and an outer hydrophilic shell. To render the micellar aggregates more stable, cross-linking of the polymeric chain was done by using N,N'methylene bis acrylamide during the vinyl polymerization process. The resulting micellar aggregate is suitable of dissolving hydrophobic drugs such as ketorolac, indomethacin and nimesulide. These micellar aggregates are very small in size (<50 nm diameter) and therefore, can easily penetrate the mucin membrane of the eye, have mucoadhesive properties and, therefore, can adhere on the corneal surface so that the corneal penetration is an extremely slow process. At and above 35° C., these nanoparticles are desolvated and becomes hydrophobic due to the presence of NIPAAM unit. This results the deposition of particles in the membrane pores and cause sustained release of the drug there.

The block copolymer micelles are made of mucoadhesive and thermosensitive polymer components, and when instilled, it penetrates the mucin membrane, adhere to the membrane pores and at body temperature, it becomes more hydrophobic to release the drug faster. These biodegradable block copolymer micelles nanoparticles having an average diameter of 20 nm to 60 nm (at 25° C.) are particularly suitable for formulating an ocular delivery composition of NSAIDs like ketorolac, indomethacin and nimesulide which are usually made soluble in water by making them salts in acidic medium.

The random block copolymer of micelles of the present invention may be prepared by mixing monomers such as vinylpyrrolidone (VP), N-isopropyl is acrylamide (NIPAAM) and acrylic acid(AA) in presence of N,N' methylene bis acrylamide (MBA) and polymerizing the mixture by free radical polymerization reaction using ammnonium persulphate as catalyst. The hydrophobic moiety of the polymeric chain remain buried inside the micelles which help dissolution of drug and the hydrophilic moiety such as carboxylic acids are extended outside the surface of the micelles. The clear solution of the micellar dispersion in aqueous solution can be instilled in the patient's eyes much more effectively and the sustained release of the drug encapsulated inside the micelles enhances the therapeutic effect of the drug.

The block copolymer used in the drug composition of the present invention may be a random copolymer of constituents VP, NIPAAM and AA.

- - - (-VP+NIPAAM+AA-)$_m$ - - - wherein, m is an integer larger than 2, preferably from 10 to 4000.

In this copolymer, the VP, NIPAAM and AA components are responsible for hydrogel formation, thermosensitivity and mucoadhesiveness of the micelles respectively.

The monomers are not limited to only these three monomers only. Any monomer having these characteristics can be used for such micelles. As for example, instead of NIPAAM, one can take N-alkylacrylamide of general formula

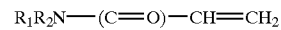

$$R_1R_2N-(C=O)-CH=CH_2$$

Wherein $R_1$ may be a proton or $C_nH_{2n+1}$ in which n may have any value from 3 to 6.

Instead of VP one can take vinylalcohol.

Suitable hydrophobic drugs, which may be incorporated into the block copolymer micelles of the present invention, are non-steroid antiinflammatory drugs such as ketorolac, indomethacin and nimesulide.

The combination of amphiphilic monomers is preferably VP, NIPAAM and AA in the molar ratio 9.5%:5.7%:4.8%

In order to incorporate one or more drugs mentioned above into the block copolymer micelles, various methods described below may be used alone or in combination.

(i) Stirring

A drug is added to an aqueous solution of a block copolymer, and stirred for 2 to 24 hours to obtain micelles containing drug.

(ii) Heating

A drug and an aqueous solution of a block copolymer are mixed and stirred at 30° C. to 80° C. for 5 minutes to a couple of hours and then cooled to room temperature while stirring to obtain micelles containing the drug.

(iii) Ultrasonic Treatment

A mixture of a drug and an aqueous solution of a block copolymer is subjected to an ultrasonic treatment for 10 minutes to 30 minutes and then stirred at room temperature to obtain micelles containing the drug.

(iv) Solvent Evaporation

A drug is dissolved in an organic solvent such as chloroform and was added to an aqueous solution of micelles. Subsequently the organic solvent was evaporated slowly while stirring, and then filtered to remove free drug.

(v) Dialysis

The polymeric micelles solution was added to an organic solution of drug and the mixture is dialyzed against a buffer solution and then water.

The micelle solution of block copolymers is prepared by dissolving amphiphilic monomers in an aqueous medium to obtain micelles, adding aqueous solutions of cross-linking agent, activator and initiator into the said micelles, subjecting the said mixture to polymerization in presence of an inert gas at 30° C.–40° C. till the polymerization of micelles is complete.

The purification step is done by dialysis. The dialysis is carried out for 2–4 hours to eliminate unreacted monomers and free NSAID, if any, in the aqueous phase.

The organic solvents used for dissolving the drug is selected from dimethylformamide (DMF), dimethylsulphoxide (DMSO), dioxane, chloroform, n-hexane, dichloromethane, ethylacetate, ethanol, methanol.

The cross linking agent is a bifunctional vinyl derivative, such as N,N' methylene bis acrylamide.

The initiators are peroxide derivatives, such as benzoyl peroxide, or perdisulphate salts like ammonium perdisulphate or 2,2'-azo bis isobutyronitrile (AIBN).

The activator is ferrous ammonium sulphate (FAS). The inert gas is nitrogen or argon. The temperature at which polymerization is carried out ranges between 20° C.–80° C., particularly between 30° C.–40° C.

A hydrophobic drug may be incorporated into the polymeric micelles of the present invention during the time of polymerization wherein the drug is dissolved into the micelles of the monomers in aqueous solution and the polymerization is done in presence of the drug.

As the drug held in the hydrophobic core of the micelles is released on the cornea surface in a controlled manner for a long time, the composition of the present invention is suitable for formulating drugs, which are not amenable to conventional formulating techniques or using non mucoadhesive micelles.

The present invention thus provides a formulation which is therapeutically more effective and toxicologically much safer, than conventional formulations of hydrophobic drugs.

The invention will now be described with reference to the following examples and the accompanying drawings.

FIG. 1—Typical size distribution of NIPAAM-VP-AA copolymeric micelles by dynamic light scattering measurement.

Figure 2:
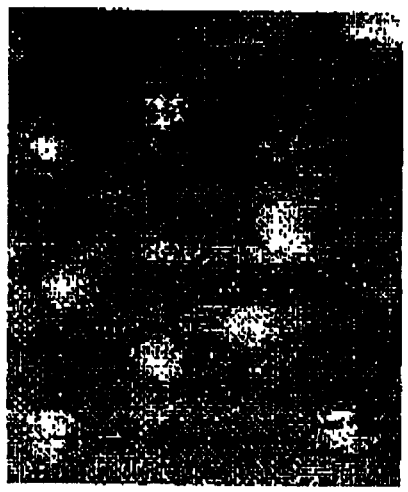

FIG. 2—Transmission electron microscope picture of keterolac loaded NIPAAM-VP-AA copolymeric micelles (scale 1 cm=5 nm).

Figure 3:
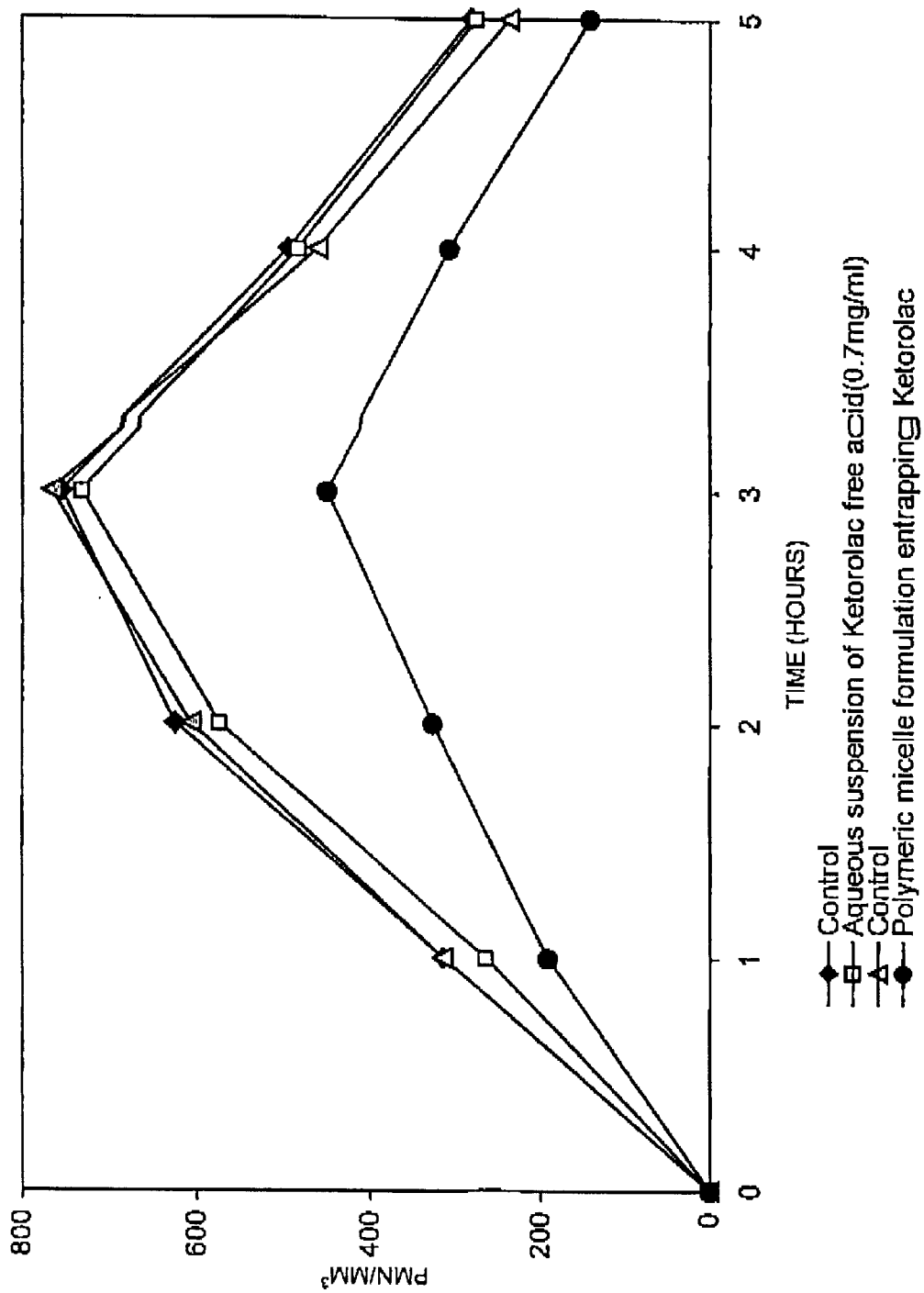

FIG. 3—Tear fluid PMN counts of keterolac formulation on $PGE_2$ induced ocular inflammation in rabbits.

FIG. 1 shows stable micelles having an average size of 30 nm to 60 nm diameter. Micelles of this size range are dispersed in water to give a transparent solution. The stability of the micelles is excellent as can be seen from the shelf life studies. The particle size was measured by Dynamic Light Scattering Experiment wherein the drug loaded lyophilized powder was dissolved in aqueous buffer to get about 5% solution. The solution was then filtered through 200 nm Millipore filter and the particle size and size distribution of the polymeric micelles was determined using a Brookhaven B18000 instrument with a B1200 SM goniometer. An aircooled argon ion laser operated at 488 nm was used as light source. The intensity of scattered light was detected at 90° to an incident beam. The measurement was done using a 128 channel digital correlator which derive the time dependent autocorrelation function of the scattered intensity. The size of the particle was calculated from diffusion of the particles using Stoke-Einstein equation. The particle size and size distribution of ketorolac loaded polymeric micelles nanoparticles are shown this figure FIG. 2 shows the transmission Electron Microscopic (TEM) picture of the stained samples of polymeric micelles loaded with ketorolac. The TEM picture of the micellar nanoparticles was taken in a Philips EM 300 instrument using 14000 times magnification. A drop of aqueous solution of lyophilized powder (~5 mg/ml) was placed on a membrane coated grid surface with a filter paper (Whatman #1). A drop of 1% phosphotungstic acid was immediately added to the surface of the grid. After 1 minute excess fluid was removed and the grid surface was air dried at room temperature before loaded in the microscope. The micelles nanoparticles are all spherical in shape and nearly monodispersed.

The invention will now be described with reference to the following examples

EXAMPLE 1

Preparation of Polymeric Nanoparticles Containing Ketorolac:

To 900 mg NIPAAM, 100 ll freshly distilled VP and 50 ll freshly distilled AA in 100 ml water, 300 ll MBA ([MBA]= 0.049 gm/ml) was added to cross-link the polymer chain. The dissolved oxygen was removed by passing nitrogen gas for 30 mins. 50 ll of 0.5% w/v ferrous ammonium sulphate (FAS) and 50 ll saturated ammonium persulphate (APS) solutions were, then, added to initiate the polymerization reaction. The polymerization was done at 30° C. for 24 hrs in nitrogen atmosphere. Total aqueous solution of polymer was then dialyzed for overnight using a spectrapore membrane dialysis bag (12 kD cut off). The dialyzed aqueous solution of polymeric micelles was frozen in liquid nitrogen and was lyophilized immediately to obtain dry powder for subsequent use. The yield of micelles nanoparticles was more than 80%. The lyophilized powder is easily redispersible in aqueous buffer. 100 mg of lyophilized powder of polymeric micelles was dispersed in 10 ml of water and was stirred well to disperse the micelles. The free acid form of ketorolac was dissolved in absolute ethanol ([ketorolac]=50 mg/ml) and the alcoholic solution was added in polymeric micelles slowly with constant stirring. Ketorolac got directly loaded into hydrophobic core of micelles. The drug loaded polymeric micelles were then lyophilized to get dry powder for subsequent use.

EXAMPLE 2

Preparation of Polymeric Nanoparticles Containing Indomethacin:

In 100 mg of the lyophilized powder of the polymeric micelles nanoparticles, an alcoholic solution of indomethacin ([Indomethacin]=33 mg/ml) was added with constant stirring to get clear solution of polymeric micelles containing the drug of desired concentration dispersed in aqueous buffer. Maximum 10% w/w of the drug could be dissolved in polymeric micelles at room temperature. The drug loaded polymeric micelles was then lyophilized to get dry powder for subsequent use.

EXAMPLE 3

Preparation of Polymeric Micelles Containing Nimesulide:

In 100 mg of dry powder of polymeric micelles, an alcoholic solution of nimesulide ([nimesulide]=10 mg/ml) was added with constant stirring to get clear solution. Maximum 8% w/w of nimesulide could be dissolved in polymeric micelles at room temperature. The drug loaded micelles was then lyophilized to get dry powder for subsequent use.

EXAMPLE 4

Measurement of Particle Size by Dynamic Light Scattering Experiment:

The drug loaded lyophilized powder was dissolved in aqueous buffer to get about 5% solution. The solution was then filtered through 200 nm Millipore filter and the particle size and size distribution of the polymeric micelles was determined using a Brookhaven B18000 instrument with a B1200 SM goniometer. An aircooled argon ion laser operated at 488 nm was used as light source. The intensity of scattered light was detected at 90° to an incident beam. The measurement was done using a 128 channel digital correlator which derive the time dependent autocorrelation function of the scattered intensity. The size of the particle was calculated from diffusion of the particles using Stoke-Einstein equation.

The particle size and size distribution of ketorolac loaded polymeric micelles nanoparticles are shown in FIG. 1. of the accompanying drawing.

EXAMPLE 5
Transmission Electron Microscopic (TEM) Picture of the Nanoparticles:

The TEM picture of the micellar nanoparticles was taken in a Philips EM 300 instrument using 14000 times magnification. A drop of aqueous solution of lyophilized powder (~5 mg/ml) was placed on a membrane coated grid surface with a filter paper (Whatman #1). A drop of 1% phosphotungstic acid was immediately added to the surface of the grid. After excess fluid was removed and the grid surface was air dried at room temperature before loaded in the microscope. The TEM picture of stained samples of polymeric micelles loaded with ketorolac is shown in FIG. 2. of the accompanying drawing. The micelles nanoparticles are all spherical in shape and nearly monodispersed.

EXAMPLE 6
Shelf Life of the Drug Loaded Polymeric Micelles Nanoparticles:

The shelf life of drug loaded polymeric micelles was determined by dissolving certain amount of drug loaded lyophilized powder in water and the solution was kept in incubator at 25° C. The solution was clear at the time of loading (zero time). The time when the solution became just turbid was noted. The shelf life of ketorolac loaded nanoparticles, for example, is shown in the table 1. The table shows that while 5% w/w ketorolac in polymeric micelles keeps the solution clear for more than 15 days, a solution containing nanoparticles of 30% loading gives turbidity within 24 hours. This shows that these drugs entrapped in polymeric micelles can not be used as aqueous solution for a very long time and has to be kept as a lyophilized powder.

In vitro Transcorneal Permeation Studies:

The experiment was carried out using freshly excised rabbit corneas. Albino rabbit weighing 1.5 to 2 kg was sacrificed with an intravenous lethal dose of phenobarbitone sodium injection (200 mg/ml) and eye balls were removed. The corneas were dissected along with 2–4 mm of surrounding scleral tissue and washed with cold normal saline water. Cornea was mounted between the donor and receptor chambers of a to modified version of Franz all glass diffusion cell. Cornea area available for permeation was 0.64 cm². The receptor was filled with 12 ml of bicarbonate ringer and all air bubbles were removed. 1 ml of formulation was placed in the donor chamber i.e. on the top of the cornea. The entire set up was thermostated at 37° C. 2 ml sample was withdrawn at 60 and is 120 mins from the receptor chamber through the sample port and was diluted with 0.1 N HCl, and the drug content was determined spectrophotometrically by measuring the absorbance at 313 nm, 319 nm or 301 nm for ketorolac, indomethacin or nimesulide respectively. Bicarbonate ringer replaced the quantity of samples withdrawn. At the end cornea was freed of scleral ring and weighed. The cornea was then dried at 80° C. to constant weight to determine the corneal hydration. Corneal hydration level was found to be between 79% and 80% as shown in table 2, indicating no corneal damage has taken place due to addition of keterolac formulation.

In vivo Studies of Keterolac Formulation on $PGE_2$ Induced Ocular Inflammation in Rabbits:

Eight albino rabbits of either sex were divided randomly into two groups of four each. Each rabbit received 50 ul of keterolac formulation in left eye and 50 ll of control vehicle (distilled water) in the contra lateral eye. Ten minutes late 50 ul of $PGE_2$ was instilled in both eyes. All eyes were then evaluated for parameters of inflammation i.e, lid closure and polymorphonuclearleukocyte (PMN) migration. Lid closure parameter was scored as follows:

0. full open,
1. one third open,
2. two third open,
3. fully closed.

Normal saline (100 ll) was instilled in the interior cul de sac of the rabbit eye and after quick and gentle mixing 50 ul of the tear fluid was withdrawn at 1,2,3,4 and 5 hours following $PGE_2$ instillation. Tear fluid PMN was counted in Neubauer haemocytometer. The result as shown in FIG. 3 of the accompanying drawing, indicated that the lid closure was prominent up to three hours after which it subsided. The lid closure was found to be more in all control eyes as compared to the eyes treated with nanoparticle formulations. Also the lid closure in case of eyes treated with nanoparticle formulations was very less compared to that observed with suspension of keterolac of same concentration (table-3). PMN counts in the tears of rabbit increased up to three hours and afterward it decreased. In case of nanoparticle formulation, the PMN counts were observed to be less than the control throughout the five hour study. The percentage inhibition on PMN migration with nanoparticle formulations was found to be much higher and longer lasting than that observed with aqueous suspension containing equivalent amount of ketorolac.

TABLE 1

Shelf-life studies of drug loaded polymeric micelles with varying amount of ketorolac

| Time | w/w % of ketorolac dissolved in aqueous solution of polymer | | | | | |
|---|---|---|---|---|---|---|
| (hours) | 5 | 10 | 15 | 20 | 25 | 30 |
| 1 | C | C | C | C | C | C |
| 2 | C | C | C | C | C | C |
| 3 | C | C | C | C | C | C |
| 4 | C | C | C | C | C | C |
| 5 | C | C | C | C | C | C |
| 6 | C | C | C | C | C | C |
| 24 | C | C | C | C | C | T |
| 48 | C | C | C | C | C | — |
| 72 | C | C | C | C | C | — |
| 96 | C | C | C | C | C | — |
| 120 | C | C | C | C | C | — |
| 144 | C | C | C | C | C | — |
| 168 | C | C | C | C | C | — |
| 192 | C | C | C | C | C | — |

C-CLEAR, T-TURBIDITY

TABLE 2

Comparison of permeation of ketorolac from NIPAAM-VP-AA copolymeric micelle formulation with aqueous suspension of drug of same concentration (0.7 mg/ml) through rabbit cornea

| Formulation | Cumulative amount of ketorolac permeated (mg □ S.E.) Values in parentheses indicate % permeation (Time) | | Corneal hydration (%) |
|---|---|---|---|
| | 60 Mins. | 120 Mins. | |
| Polymeric micellar formulation | 0.04896 ± 0.00094 (6.9942%) | 0.06576 ± 0.00089 (9.3942%) | 80.19 ± 0.199 |
| Aqueous suspension of ketorolac | 0.02736 ± 0.00087 (3.9085%) | 0.03624 ± 0.00092 (5.1771%) | 79.41 ± 0.0899 |

TABLE 3

Comparison of effect of ketorolac loaded NIPAAM-VP-AA copolymeric micelle formulation with aqueous suspension of drug of same concentration on $PGE_2$ induced lid closure in rabbit eye

| Formulation | 30 Min | 1 hr | 2 hr | 3 hr | 4 hr | 5 hr |
|---|---|---|---|---|---|---|
| (1) Control Formulation = Aqueous suspension of Ketorolac free acid (0.7 mg/ml) N = 4 | 1.75 ± 0.25 1.66 ± 0.202 | 1.75 ± 0.25 1.66 ± 0.202 | 1.66 ± 0.2974 1.66 ± 0.2974 | 0.5 ± 0.25 0.5 ± 0.25 | 0.5 ± 0.2165 0.5 ± 0.2165 | 0 0 |
| (1) Control Formulation = Polymeric micellar formulation N = 4 | 1.75 ± 0.25 0.5 ± 0.25 | 1.75 ± 0.25 0.5 ± 0.25 | 1.75 ± 0.25 0.5 ± 0.25 | 1.75 ± 0.25 0.5 ± 0.25 | 1.75 ± 0.25 0 | 0 0 |

We claim:

1. A sustained release and long residing ophthalmic formulation comprising:
    a micelle solution of block random co-polymer having a hydrophobic component and a hydrophilic component of general formula —(X+Y+Z-)$_m$,
    wherein
    m is an integer greater than 2,
    X is a monomer which will provide hydrogel formulation properties of the co-polymer to reduce the irritability of the eye and is selected from vinyl group of compounds,
    Y is a monomer which will provide thermo-sensitivity properties of the co-polymer having a general formula $R_1$—$R_2$N—(C=O)—CH=$CH_2$, where
        $R_1$ a proton or $C_nH_{2n+1}$ in which n may have the value from 3 to 6 and
        $R_2$=alkyl group having chain length of $C_3$ to $C_6$, and
    Z is a monomer which will provide mucoadhesiveness and pH-sensitivity properties to the co-polymer and is selected from acrylate based monomers; and
    at least one hydrophobic drug entrapped within the micelles.

2. A formulation as claimed in claim 1 wherein, said vinyl group of compounds is selected from vinyl pyrrolidone, vinyl alcohol, vinyl chloride or vinyl acetate.

3. A formulation as claimed in claim 1 wherein, Y is N-isopropyl acrylamide (NIPAAM).

4. A formulation as claimed in claim 1 wherein said acrylate based monomer is selected from acrylic acid or methyl methacrylate.

5. A formulation as claimed in claim 1 wherein, m lies in the range 10–4000.

6. A formulation as claimed in claim 1 wherein, said drug is non steroidal anti inflammatory drug (NSAID).

7. A formulation as claimed in claim 6 wherein, said NSAID drug is selected from 5-benzoyl (2,3 dihydro-1H pyrrolizone-1 carboxylic acid), (ketorolac); 1-(4 chlorobenzoyl)-5 methoxy-2-methyl-1H-indole-3-acetic acid (indomethacin) or N-(4-nitro-2 phenoxyphenyl) methanesulphonamide (nimesulide) or a mixture of at least any two thereof.

8. A formulation as claimed in claim 7, wherein said hydrophobic drug is in solution or in powder form.

9. A formulation as claimed in claim 1 wherein, said micelles containing the hydrophobic drug are polymerized micelles having a size in the range of 10 nm–100 nm diameter.

10. A formulation as claimed in claim 9 wherein said polymerized micelles containing the hydrophobic drug have a size in the range of 10 nm to 50 nm.

11. A formulation as claimed in claim 1 wherein, the block copolymers, made of amphiphilic monomers, are biocompatible and non-antigenic materials.

12. A formulation as claimed in claim 1 wherein the optimum molar ratio of the combination of amphiphilic monomers X, Y and Z is 9.5%:85.7%:4.8% respectively.

13. A process for preparing a sustained release and long residing ophthalmic formulation comprising the steps of:
    preparing micelle solution of block random co-polymer having a hydrophobic component and a hydrophilic component of general formula —(X+Y+Z-)$_m$, wherein
    m is an integer greater than 2,
    X is a monomer which will provide hydrogel formulation properties of the co-polymer to reduce the irritability of the eye and is selected from vinyl group of compounds,
    Y is a monomer which will provide thermo-sensitivity properties of the co-polymer having a general formula $R_1$—$R_2$N—(C=O)—CH=$CH_2$, where $R_1$=a proton or $C_nH_{2n+1}$ in which n may have the value from 3 to 6 and $R_2$=alkyl group having chain length of $C_3$ to $C_6$, and Z is a monomer which will provide mucoadhesiveness and pH-sensitivity properties to the co-polymer and is selected from acrylate based monomers; and mixing at least one hydrophobic drug with said micelle solution;

subjecting the resulting mixture to stirring, heating, ultrasonic treatment, solvent evaporation or dialysis to physically incorporate the hydrophobic drug into the hydrophobic core of block co-polymeric micelle; and purifying the mixture to recover the sustained release and long residing ophthalmic formulation.

14. A process as claimed in claim 13 wherein, said micelle solution of block copolymers is prepared by:

dissolving amphiphilic monomers in an aqueous medium to obtain micelles, adding aqueous solutions of cross-linking agent, activator and initiator into the said micelles, and subjecting the said mixture to polymerization in presence of an inert gas at 30° C.–40° C. till the polymerization of micelles is complete.

15. A process as claimed in claim 13 wherein, said vinyl group of compounds is selected from vinyl pyrrolidone, vinyl alcohol, vinyl chloride or vinyl acetate.

16. A process as claimed in claim 13 wherein, Y is N-isopropyl acrylamide.

17. A process as claimed in claim 13 wherein, said acrylate based monomers is selected from acrylic acid or methyl methacrylate.

18. A process as claimed in claim 13 wherein, m lies in the range 10–4000.

19. A process as claimed in claim 13 wherein, said purification is done by dialysis.

20. A process as claimed in claim 13 wherein, said hydrophobic drug is non steroidal anti inflammatory drug (NSAID).

21. A process as claimed in claim 20 wherein, said NSAID drug is selected from 5-benzoyl (2,3 dihydro-1H pyrrolizone-1 carboxylic acid) (ketorolac); 1-(4 chlorobenzoyl)-5 methoxy-2-methyl-1H-indole-3 acetic acid (indomethacin) or N-(4-nitro-2 phenoxyphenyl) methanesulphonamide (nimesulide) or a mixture thereof or a mixture of at least any two drugs.

22. A process as claimed in claim 13 wherein, said polymerized micelles containing the hydrophobic drug have a size in the range of 10 nm–100 nm diameter.

23. A process as claimed in claim 22 wherein, said polymerized micelles containing the hydrophobic drug have a size in the range of 10 nm to 50 nm.

24. A process as claimed in claim 13 wherein, the block copolymers, made of amphiphilic monomers, are biocompatible and non-antigenic materials.

25. A process as claimed in claim 13 wherein said hydrophobic drug is in solution form or in powder form.

26. A process as claimed in claim 13 wherein said hydrophobic drug is dissolved in a solvent selected from the group consisting of dimethylformamide (DMF), dimethylsulphoxide (DMSO), dioxane, chloroform, n-hexane, dichloromethane, ethylacetate, ethanol, and methanol.

27. A process as claimed in claim 13 wherein, said dialysis is carried out for 2–4 hours to eliminate un-reacted monomers and free NSAID, if any, at the aqueous phase.

28. A process as claimed in claim 13 wherein, said drug is in hydrophobic form.

29. A process as claimed in claim 14 wherein, said cross-linking agent is a bifunctional vinyl derivative.

30. A process as claimed in claim 29 wherein, said bifunctional vinyl derivative is N,N' methylene bis acrylamide.

31. A process as claimed in claim 14 wherein, said initiators are peroxide derivatives or 2,2'-azo bis isobutyronitrile (AIBN).

32. A process as claimed in claim 31 wherein, said peroxide derivatives are benzoyl peroxide, or perdisulphate salts like ammonium perdisulphate.

33. A process as claimed in claim 14 wherein, said activator is ferrous ammonium sulphate (FAS).

34. A process as claimed in claim 14 wherein, said inert gas is nitrogen or argon.

35. A process as claimed in claim 13 wherein the optimum combination of amphiphilic monomers is VP, NIPAAM and AA in the molar ratio 9.5%:85.7%:4.8%.

36. A process as claimed in claim 14 wherein, the temperature at which polymerization is carried out ranges between 20° C.–80° C.

37. A process as claimed in claim 36 wherein, the temperature at which polymerization is carried out ranges between 30° C.–40° C.

38. A method for ophthalmic delivery of a hydrophobic drug, the method comprising administering to a patient an eye drop comprising the ophthalmic formulation of claim 1.

* * * * *